US00PP34808P3

(12) United States Plant Patent
Olesen

(10) Patent No.: US PP34,808 P3
(45) Date of Patent: Dec. 13, 2022

(54) MINIATURE ROSE PLANT NAMED 'POULTY027'

(50) Latin Name: *Rosa hybrida*
Varietal Denomination: Poulty027

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,627

(22) Filed: Sep. 7, 2021

(65) Prior Publication Data

US 2022/0104416 P1 Mar. 31, 2022

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 120, 121
See application file for complete search history.

(56) References Cited

PUBLICATIONS https://www.poulsenroser.dk/de/roses/ShowProduct/68762?productGroup=PAY (Retrieved from the Internet on May 5, 2022) (2 pages total).*

* cited by examiner

*Primary Examiner* — Susan McCormick Ewoldt

(57) ABSTRACT

A new garden rose plant of the Miniature class which has abundant, coral pink flowers and attractive foliage. This new and distinct variety has shown to be uniform and stable in the resulting generations from asexual propagation.

1 Drawing Sheet

Botanical designation: *Rosa hybrida.*
Variety denomination: 'Poulty027'.

This application claims priority to Plant Breeder's Rights Application Number 2020/2275, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulty027', originated as a single seedling from the stated cross.

The new variety may be distinguished from its male pollen parent and female seed parent primarily by the following characteristics. The male pollen parent plant grows to 100 cm tall in one season, while the new variety grows to about 33 cm in height during one growing season. The female seed parent plant has light red flowers while the new variety has coral pink flowers.

The objective of the hybridization of this rose variety was to create a new and distinct variety with unique qualities, such as:

1. Uniform and abundant coral pink flowers;
2. Vigorous, but compact growth when propagated on its own roots;
3. Exceptional disease resistance.

This combination of qualities is not present in previously available commercial cultivars of this type, known to the inventor, and distinguish 'Poulty027' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulty027' was selected in the spring of 2014 by the inventor as a single plant from the progeny of the aforementioned hybridization.

Asexual reproduction of 'Poulty027' by rooted cuttings was first done by Mogens N. Olesen in the nursery in Fredensborg, Denmark in July, 2014. This initial and other subsequent asexual propagations conducted in controlled environments have demonstrated that the characteristics of 'Poulty027' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty027'. Specifically illustrated in the drawing are a flowering branch, open flower viewed from above, a partially opened flower viewed from the side, bare stem, leaves, petals detached, and sepals detached revealing reproductive flower parts. Plants shown are 4 months in age.

DETAILED DESCRIPTION OF THE VARIETY

The following is a description of 'Poulty027', as observed in its growth in a greenhouse in Odense Denmark. Plants were grown in 19 cm containers under natural light conditions, for a period of 4 months.

For a comparison, several physical characteristics of the rose variety 'Poulpar056', U.S. Plant Pat. No. 23,603 are compared to 'Poulty027' in Chart 1.

CHART 1

| | 'Poulty027' | 'Poulpar056' |
|---|---|---|
| Petal Count | 35 | 65 |
| Flower Diameter | 34 mm | 50 to 60 mm |
| General Tonality of Flower Color | Open flowers are Red Group 52B, Red-Purple Group 58B after flowers have fully matured | Red Group 38A with intonations of Red Group 55B. |

FLOWER AND FLOWER BUD

Blooming habit: Continuous.

Flower bud:

*Size.*—Upon opening, 21 mm in length from base of receptacle to end of bud. Bud diameter is 15 mm.

*Bud form.*—Ovoid.

*Bud color.*—As sepals divide petals are Red Group 53C.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—21 mm long, 8 mm wide.

*Receptacle.*—Texture: Smooth. Size: 6 mm in height, 10 mm wide. Color: Yellow-Green Group 144A. Shape: Funnel.

*Pedicel.*—Surface: Smooth. Length: 35 mm. Diameter: 2 mm on average. Color: Yellow-Green Group 144B. Strength: Strong.

*Peduncle.*—Length: 1.5 to 8 cm. Diameter: About 3 mm. Color: Yellow-Green Group 144A. Texture: Smooth.

Flower bud development: Flower buds are borne in clusters of 5 flower buds per stem on average.

Flower bloom:

*Fragrance.*—None.

*Duration.*—The blooms have a duration on the plant of approximately 21 days. Petals fall cleanly away from plant after flowers have fully matured.

*Size.*—Flower diameter is 34 mm when open. Flower depth is 15 mm.

*Flower shape.*—High centered, double, with a high pointed center which is tightly closed.

*Shape of flower, side view.*—The upper portion is flat. The lower portion is flat.

Petalage: Under normal conditions, flowers have about 35 petals.

General tonality of flower: Open flowers are Red Group 52B. Red-Purple Group 58B after flowers have fully matured.

Petal color:

*Upon opening, outer petals.*—Upper surface: Red Group 52A. At basal zone intonations of Red Group 38C. At the basal point of attachment Yellow Group 12B. Lower surface: Red Group 53C with streaks Red Group 55D.

*Upon opening, inner petals.*—Upper surface: Red Group 46B with intonations of Red Group 38B at the middle zone. Basal petal spot Yellow Group 12B. Lower surface: Red Group 50A with a basal petal spot of Yellow 12B.

Petals:

*Petal reflex.*—Partial reflex at the margin.

*Margin.*—Entire and uniform. Moderate undulations.

*Shape.*—Broad and elliptic. Apex shape: Rounded. Base shape: Acute.

*Size.*—29 mm (l)×30 mm (w).

*Texture.*—Smooth.

*Thickness.*—Average.

Petaloids:

*Size.*—4 mm (l) by 4 mm (w).

*Quantity.*—About 6.

*Shape.*—Elliptical with an acute base and rounded apex.

*Color.*—Red Group 46B on the upper surface and Red Group 50A underneath.

Reproductive flower parts:

*Pollen.*—None observed.

*Anthers.*—Size: 1.5 mm in length. Color: Yellow Group 13B. Quantity: 38 on average.

*Filaments.*—Color: Yellow Group 11A. Length: 4 mm.

*Pistils.*—Length: 4 mm. Quantity: 20 on average.

*Stigmas.*—Color: Greyed-Yellow Group 160D.

*Styles.*—Color: Yellow-Green Group 157D.

*Location of stigmas.*—Inferior in location relative to the length of the filaments and the height of the anthers.

*Hips.*—None Observed.

PLANT

Plant growth: Upright, bushy, and very compact. Plants are 33 cm in height, and 33 cm wide.

Stems:

*Color of juvenile growth.*—Yellow-Green Group 144B.

*Color of mature growth.*—Yellow-Green Group 144A.

*Length.*—Canes are about 10 cm from the base of the plant to the flowering portion.

*Diameter.*—About 3.5 mm.

*Internodes.*—On mature canes about 31 mm between nodes.

*Surface texture.*—Young wood: Smooth. Older wood: Smooth.

Long prickles: None observed.

Plant foliage:

*Compound leaf.*—About 105 mm (l)×60 (w).

*Quantity.*—3 or 4 leaves per 10 cm of stem on average.

*Leaf bearing angle to the stem.*—45 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 7 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 1.5 mm. Upper surface color: Yellow-Green Group 144A. Lower surface color: Yellow-Green Group 144A.

*Rachis*.—Length: 35 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 40 mm long, 22 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae,* downy mildew *Peronospora sparsa,* rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulty027', substantially as illustrated and described herein, due to its abundant coral pink flowers, disease resistance, and extended period of bloom.

* * * * *

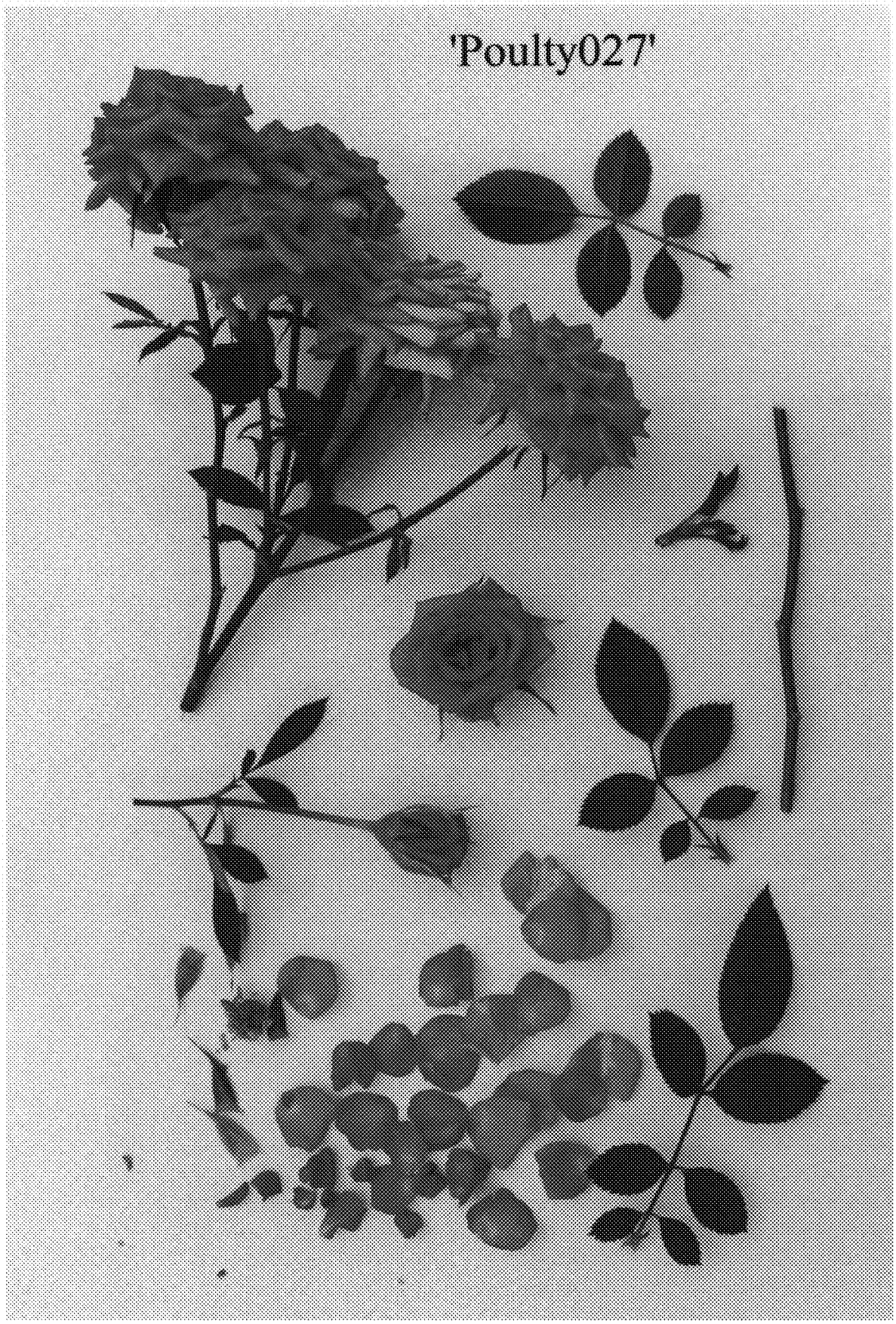
'Poulty027'